(12) United States Patent
Rummel

(10) Patent No.: US 8,293,230 B2
(45) Date of Patent: Oct. 23, 2012

(54) TRANSPORT PROTEIN WHICH IS USED TO INTRODUCE CHEMICAL COMPOUNDS INTO NERVE CELLS

(75) Inventor: Andreas Rummel, Garbsen (DE)

(73) Assignee: TOXOGEN GmbH, Langenhagen (DE)

( * ) Notice: Subject to any disclaimer, the term of this patent is extended or adjusted under 35 U.S.C. 154(b) by 460 days.

(21) Appl. No.: 11/661,849

(22) PCT Filed: Sep. 6, 2005

(86) PCT No.: PCT/EP2005/009554
§ 371 (c)(1),
(2), (4) Date: May 9, 2007

(87) PCT Pub. No.: WO2006/027207
PCT Pub. Date: Mar. 16, 2006

(65) Prior Publication Data
US 2007/0299008 A1    Dec. 27, 2007

(30) Foreign Application Priority Data

Sep. 6, 2004  (DE) .................. 10 2004 043 009

(51) Int. Cl.
*A61K 38/48* (2006.01)
(52) U.S. Cl. ............... 424/94.63; 530/300; 530/350; 435/219
(58) Field of Classification Search .................. None
See application file for complete search history.

(56) References Cited

U.S. PATENT DOCUMENTS

| | | | |
|---|---|---|---|
| 7,273,722 B2 * | 9/2007 | Lin et al. ............... | 435/69.1 |
| 7,456,272 B2 * | 11/2008 | Lin et al. ............... | 536/23.7 |
| 7,556,817 B2 * | 7/2009 | Steward et al. ......... | 424/239.1 |
| 7,563,874 B2 * | 7/2009 | Marks et al. ........... | 530/388.15 |
| 2004/0175385 A1 * | 9/2004 | Marks et al. ........... | 424/164.1 |
| 2008/0050352 A1 * | 2/2008 | Webb et al. ............ | 424/93.41 |
| 2008/0102090 A1 * | 5/2008 | Panjwani et al. ....... | 424/239.1 |

FOREIGN PATENT DOCUMENTS

| | | | |
|---|---|---|---|
| GB | 2416692 | * | 8/2006 |
| WO | WO 00/55208 | | 9/2000 |

OTHER PUBLICATIONS

Ihara, H et al, Sequence of the gene for *Clostridium botulinum* type B neurotoxin associated with infant botulism, expression of the C-terminal half of the heavy chain and its binding activity, Biochimica et Biophysica ACTA, Gene Structure and Expression, Elsevier, Amsterdam, NL, vol. 1625, No. 1, Jan. 3, 2003, pp. 19-26, Figures 1-3.*
Swiss Prot accession No. Q45894, *Clostridium botulinum* toxin type A.*
Swiss-Prot accession No. Q3LRX9, *Clostridium botulinum* toxin type A.*
Willems, A et al, Research Microbiology, 1993, vol. 144(7), pp. 547-556, Sequence of the gene coding for the neurotoxin of *Clostridium botulinum* type A associated with infant botulism: comparison with other clostridial neurtoxins.*
East, International Journal of Systematic Bacteriology, vol. 46(6), pp. 1105-1112, Oct. 1996.*
Rummel, A et al, Molecular Microbiology, vol. 51(3), pp. 631-643, 1004.*
Louch, HA et al, Biochemistry, vol. 41, pp. 13644-13652, 2002.*
Willems et al, Res. Microbiology, 1993, vol. 144, pp. 547-556.*
Ihara, H., et al., "Sequence of the Gene for *Clostridium botulinum* Type B Neurotoxin Associated with Infant Botulism, Expression of the C-terminal Half of Heavy Chain and its Binding Activity," Biochimica et Biophysica Acta 1625:19-26 (2003).
Willems, A. et al., Botulinum neurotoxin type A—*Clostridium botulinum*, Accession No. I40645.
Maksymowych, A.B. and Simpson, L.L., "Structural Features of Botulinum Neurotoxin Molecule that Govern Binding and Transcytosis Across Polarized Human Intestinal Epithelial Cells", *J. Pharma. and Exp. Thera.*, Abstract (2004).
Ihara H, et al., "Sequence of the gene for *Clostridium botulinum* type B neurotoxin associated with infant botulism, expression of the C-terminal half of heavy chain and its binding activity," *Biochimica et biophysica Acta* 1625 (2003) 19-26.
Ginalski K, et al., "Structure-based sequence alignment for the β-trefoil subdomain of the clostridium neurotoxin family provides residue level information about the putative ganglioside binding site," *IFEBS Letters* 482 (2000) 119-124.
Goodnough MC, et al., "Development of a delivery vehicle for intracellular transport of butlinum neurotoxin antagonists," *FEBS Letters* 513 (2002) 163-168.
Rummel a, et al., "The Hcc-domanin of butulinum neurotoxins A and B exhibits a singular ganglioside binding site displaying serotype specific carbohydrate interaction," *Molecular Microbiology* (2004) 51(3), 631-643.
Sutton JM, et al., "Tyrosine-1290 of tetanus neurotoxin plays a key role in its binding to gangliosides and functional binding to neurones," *FEBS Letters* 493 (2001) 45-49.
Rummel, et al., "The $H_{cc}$-domain of botulinum neurotoxins A and B exhibits a singular ganglioside binding site displaying serotype specific carbohydrate interation," *Molecular Microbiology*, vol. 51 (No. 3, pp. 631-643 (2004).
Nihon Saikingaku Zasshi, vol. 57, No. 1, pp. 245, 2053 (2002).
Ihara et al., "Sequence of the gene for *Clostridium botulinum* type B neurotoxin associated with infant botulism, expression of the C-terminal half of heavy chain and its binding activity," *Biochimica et Biophysica Acta*, vol. 1625,pp. 19-25 (2003).
Ginalski et al., "Structure-based sequence alignment for the β-trefoil subdomain of the clostridial neurotoxin family provides residue level information about the putative ganglioside binding site," *FEBS Letters*, vol. 482, pp. 119-124 (2000).

* cited by examiner

*Primary Examiner* — Patricia A Duffy
(74) *Attorney, Agent, or Firm* — McCarter & English, LLP; Steven G. Davis; Jin Wang, Esq.

(57) ABSTRACT

The invention relates to a transport protein which can be obtained by modifying the heavy chain of the neurotoxin formed by *Clostridium botulinum*. The protein binds specifically to nerve cells with a higher affinity as the native neurotoxin. The invention also relates to a method for the production of transport protein, the nucleic acids coding for the transport protein, the transport protein containing pharmaceutical and cosmetic compositions and use thereof.

17 Claims, 5 Drawing Sheets

%-binding of BoNT/A Hc-fragment hybrids vs. wild type

Figure 4

SEQUENCE LISTING

<160> NUMBER OF SEQ ID NOS: 13

<210> SEQ ID NO 1
<211> LENGTH: 1296
<212> TYPE: PRT
<213> ORGANISM: Clostridium botulinum
<220> FEATURE:
<223> OTHER INFORMATION: neurotoxin type A
<300> PUBLICATION INFORMATION:

<308> DATABASE ACCESSION NUMBER: VERSION AAA23262.1  GI:144865

<400> SEQUENCE: 1

```
Met Pro Phe Val Asn Lys Gln Phe Asn Tyr Lys Asp Pro Val Asn Gly
 1               5                   10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
```

```
                    405                 410                 415
Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
                530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Met Phe Leu Gly Trp Val Glu
                595                 600                 605

Gln Leu Val Tyr Asp Phe Thr Asp Glu Thr Ser Glu Val Ser Thr Thr
                610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
                690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
                820                 825                 830
```

-continued

```
Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
        930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
            995                1000                1005

Asp Tyr Ile Asn Arg Trp Ile Phe Val Thr Ile Thr Asn Asn Arg
        1010                1015                1020

Leu Asn Asn Ser Lys Ile Tyr Ile Asn Gly Arg Leu Ile Asp Gln
        1025                1030                1035

Lys Pro Ile Ser Asn Leu Gly Asn Ile His Ala Ser Asn Asn Ile
        1040                1045                1050

Met Phe Lys Leu Asp Gly Cys Arg Asp Thr His Arg Tyr Ile Trp
        1055                1060                1065

Ile Lys Tyr Phe Asn Leu Phe Asp Lys Glu Leu Asn Glu Lys Glu
        1070                1075                1080

Ile Lys Asp Leu Tyr Asp Asn Gln Ser Asn Ser Gly Ile Leu Lys
        1085                1090                1095

Asp Phe Trp Gly Asp Tyr Leu Gln Tyr Asp Lys Pro Tyr Tyr Met
        1100                1105                1110

Leu Asn Leu Tyr Asp Pro Asn Lys Tyr Val Asp Val Asn Asn Val
        1115                1120                1125

Gly Ile Arg Gly Tyr Met Tyr Leu Lys Gly Pro Arg Gly Ser Val
        1130                1135                1140

Met Thr Thr Asn Ile Tyr Leu Asn Ser Ser Leu Tyr Arg Gly Thr
        1145                1150                1155

Lys Phe Ile Ile Lys Lys Tyr Ala Ser Gly Asn Lys Asp Asn Ile
        1160                1165                1170

Val Arg Asn Asn Asp Arg Val Tyr Ile Asn Val Val Val Lys Asn
        1175                1180                1185

Lys Glu Tyr Arg Leu Ala Thr Asn Ala Ser Gln Ala Gly Val Glu
        1190                1195                1200

Lys Ile Leu Ser Ala Leu Glu Ile Pro Asp Val Gly Asn Leu Ser
        1205                1210                1215

Gln Val Val Val Met Lys Ser Lys Asn Asp Gln Gly Ile Thr Asn
        1220                1225                1230

Lys Cys Lys Met Asn Leu Gln Asp Asn Asn Gly Asn Asp Ile Gly
        1235                1240                1245
```

```
Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 2
<211> LENGTH: 213
<212> TYPE: PRT
<213> ORGANISM: Clostridium botulinum
<220> FEATURE:
<223> OTHER INFORMATION: Amino acids 1079 to 1291 of neurotoxin type B
<300> PUBLICATION INFORMATION:
<308> DATABASE ACCESSION NUMBER: VERSION AAA23211.1  GI:144735

<400> SEQUENCE: 2

Ser Tyr Ser Glu Tyr Leu Lys Asp Phe Trp Gly Asn Pro Leu Met Tyr
1               5                   10                  15

Asn Lys Glu Tyr Tyr Met Phe Asn Ala Gly Asn Lys Asn Ser Tyr Ile
            20                  25                  30

Lys Leu Lys Lys Asp Ser Pro Val Gly Glu Ile Leu Thr Arg Ser Lys
        35                  40                  45

Tyr Asn Gln Asn Ser Lys Tyr Ile Asn Tyr Arg Asp Leu Tyr Ile Gly
    50                  55                  60

Glu Lys Phe Ile Ile Arg Arg Lys Ser Asn Ser Gln Ser Ile Asn Asp
65                  70                  75                  80

Asp Ile Val Arg Lys Asp Tyr Ile Tyr Leu Asp Phe Phe Asn Leu
                85                  90                  95

Asn Gln Glu Trp Arg Val Tyr Thr Tyr Lys Tyr Phe Lys Lys Glu Glu
            100                 105                 110

Glu Lys Leu Phe Leu Ala Pro Ile Ser Asp Ser Asp Glu Phe Tyr Asn
        115                 120                 125

Thr Ile Gln Ile Lys Glu Tyr Asp Glu Gln Pro Thr Tyr Ser Cys Gln
    130                 135                 140

Leu Leu Phe Lys Lys Asp Glu Glu Ser Thr Asp Glu Ile Gly Leu Ile
145                 150                 155                 160

Gly Ile His Arg Phe Tyr Glu Ser Gly Ile Val Phe Glu Glu Tyr Lys
                165                 170                 175

Asp Tyr Phe Cys Ile Ser Lys Trp Tyr Leu Lys Glu Val Lys Arg Lys
            180                 185                 190

Pro Tyr Asn Leu Lys Leu Gly Cys Asn Trp Gln Phe Ile Pro Lys Asp
        195                 200                 205

Glu Gly Trp Thr Glu
    210

<210> SEQ ID NO 3
<211> LENGTH: 199
<212> TYPE: PRT
<213> ORGANISM: Clostridium botulinum
<220> FEATURE:
<223> OTHER INFORMATION: Amino acids 1093 to 1291 of neurotoxin type C1
<300> PUBLICATION INFORMATION:
<308> DATABASE ACCESSION NUMBER: VERSION CAA51313.1  GI:516175

<400> SEQUENCE: 3

Gln Tyr Thr Asn Val Val Lys Asp Tyr Trp Gly Asn Asp Leu Arg Tyr
```

-continued

```
                 1               5              10              15
Asn Lys Glu Tyr Tyr Met Val Asn Ile Asp Tyr Leu Asn Arg Tyr Met
                20              25              30

Tyr Ala Asn Ser Arg Gln Ile Val Phe Asn Thr Arg Arg Asn Asn Asn
                35              40              45

Asp Phe Asn Glu Gly Tyr Lys Ile Ile Ile Lys Arg Ile Arg Gly Asn
    50              55              60

Thr Asn Asp Thr Arg Val Arg Gly Gly Asp Ile Leu Tyr Phe Asp Met
65              70              75              80

Thr Ile Asn Asn Lys Ala Tyr Asn Leu Phe Met Lys Asn Glu Thr Met
                85              90              95

Tyr Ala Asp Asn His Ser Thr Glu Asp Ile Tyr Ala Ile Gly Leu Arg
                100             105             110

Glu Gln Thr Lys Asp Ile Asn Asp Asn Ile Ile Phe Gln Ile Gln Pro
                115             120             125

Met Asn Asn Thr Tyr Tyr Tyr Ala Ser Gln Ile Phe Lys Ser Asn Phe
                130             135             140

Asn Gly Glu Asn Ile Ser Gly Ile Cys Ser Ile Gly Thr Tyr Arg Phe
145             150             155             160

Arg Leu Gly Gly Asp Trp Tyr Arg His Asn Tyr Leu Val Pro Thr Val
                165             170             175

Lys Gln Gly Asn Tyr Ala Ser Leu Leu Glu Ser Thr Ser Thr His Trp
                180             185             190

Gly Phe Val Pro Val Ser Glu
                195

<210> SEQ ID NO 4
<211> LENGTH: 197
<212> TYPE: PRT
<213> ORGANISM: Clostridium botulinum
<220> FEATURE:
<223> OTHER INFORMATION: Amino acids 1080 to 1276 of neurotoxin type D
<300> PUBLICATION INFORMATION:
<308> DATABASE ACCESSION NUMBER: VERSION CAA38175.1  GI:40396

<400> SEQUENCE: 4

Ile Leu Arg Asn Val Ile Lys Asp Tyr Trp Gly Asn Pro Leu Lys Phe
1               5               10              15

Asp Thr Glu Tyr Tyr Ile Ile Asn Asp Asn Tyr Ile Asp Arg Tyr Ile
                20              25              30

Ala Pro Glu Ser Asn Val Leu Val Leu Val Gln Tyr Pro Asp Arg Ser
                35              40              45

Lys Leu Tyr Thr Gly Asn Pro Ile Thr Ile Lys Ser Val Ser Asp Lys
    50              55              60

Asn Pro Tyr Ser Arg Ile Leu Asn Gly Asp Asn Ile Ile Leu His Met
65              70              75              80

Leu Tyr Asn Ser Arg Lys Tyr Met Ile Ile Arg Asp Thr Asp Thr Ile
                85              90              95

Tyr Ala Thr Gln Gly Gly Glu Cys Ser Gln Asn Cys Val Tyr Ala Leu
                100             105             110

Lys Leu Gln Ser Asn Leu Gly Asn Tyr Gly Ile Gly Ile Phe Ser Ile
                115             120             125

Lys Asn Ile Val Ser Lys Asn Lys Tyr Cys Ser Gln Ile Phe Ser Ser
                130             135             140

Phe Arg Glu Asn Thr Met Leu Leu Ala Asp Ile Tyr Lys Pro Trp Arg
145             150             155             160
```

```
Phe Ser Phe Lys Asn Ala Tyr Thr Pro Val Ala Val Thr Asn Tyr Glu
                165                 170                 175

Thr Lys Leu Leu Ser Thr Ser Ser Phe Trp Lys Phe Ile Ser Arg Asp
            180                 185                 190

Pro Gly Trp Val Glu
        195

<210> SEQ ID NO 5
<211> LENGTH: 186
<212> TYPE: PRT
<213> ORGANISM: Clostridium botulinum
<220> FEATURE:
<223> OTHER INFORMATION: Amino acids 1067 to 1252 of neurotoxin type E
<300> PUBLICATION INFORMATION:
<308> DATABASE ACCESSION NUMBER: VERSION CAA44558.1  GI:40398

<400> SEQUENCE: 5

Pro Asn Thr Asn Ile Leu Lys Asp Phe Trp Gly Asn Tyr Leu Leu Tyr
1               5                   10                  15

Asp Lys Glu Tyr Tyr Leu Leu Asn Val Leu Lys Pro Asn Asn Phe Ile
            20                  25                  30

Asp Arg Arg Lys Asp Ser Thr Leu Ser Ile Asn Asn Ile Arg Ser Thr
        35                  40                  45

Ile Leu Leu Ala Asn Arg Leu Tyr Ser Gly Ile Lys Val Lys Ile Gln
50                  55                  60

Arg Val Asn Asn Ser Ser Thr Asn Asp Asn Leu Val Arg Lys Asn Asp
65                  70                  75                  80

Gln Val Tyr Ile Asn Phe Val Ala Ser Lys Thr His Leu Phe Pro Leu
                85                  90                  95

Tyr Ala Asp Thr Ala Thr Thr Asn Lys Glu Lys Thr Ile Lys Ile Ser
            100                 105                 110

Ser Ser Gly Asn Arg Phe Asn Gln Val Val Val Met Asn Ser Val Gly
        115                 120                 125

Asn Asn Cys Thr Met Asn Phe Lys Asn Asn Asn Gly Asn Asn Ile Gly
130                 135                 140

Leu Leu Gly Phe Lys Ala Asp Thr Val Val Ala Ser Thr Trp Tyr Tyr
145                 150                 155                 160

Thr His Met Arg Asp His Thr Asn Ser Asn Gly Cys Phe Trp Asn Phe
                165                 170                 175

Ile Ser Glu Glu His Gly Trp Gln Glu Lys
            180                 185

<210> SEQ ID NO 6
<211> LENGTH: 185
<212> TYPE: PRT
<213> ORGANISM: Clostridium butyricum
<220> FEATURE:
<223> OTHER INFORMATION: Amino acids 1067 to 1251 of neurotoxin type E
<300> PUBLICATION INFORMATION:
<308> DATABASE ACCESSION NUMBER: VERSION CAA43998.1  GI:40380

<400> SEQUENCE: 6

Pro Asn Ala Asn Ile Leu Lys Asp Phe Trp Gly Asn Tyr Leu Leu Tyr
1               5                   10                  15

Asp Lys Glu Tyr Tyr Leu Leu Asn Val Leu Lys Pro Asn Asn Phe Ile
            20                  25                  30

Asn Arg Arg Thr Asp Ser Thr Leu Ser Ile Asn Asn Ile Arg Ser Thr
        35                  40                  45

Ile Leu Leu Ala Asn Arg Leu Tyr Ser Gly Ile Lys Val Lys Ile Gln
50                  55                  60
```

```
Arg Val Asn Asn Ser Ser Thr Asn Asp Asn Leu Val Arg Lys Asn Asp
 65                  70                  75                  80

Gln Val Tyr Ile Asn Phe Val Ala Ser Lys Thr His Leu Leu Pro Leu
                 85                  90                  95

Tyr Ala Asp Thr Ala Thr Thr Asn Lys Glu Lys Thr Ile Lys Ile Ser
            100                 105                 110

Ser Ser Gly Asn Arg Phe Asn Gln Val Val Met Asn Ser Val Gly
        115                 120                 125

Asn Cys Thr Met Asn Phe Lys Asn Asn Gly Asn Asn Ile Gly Leu
    130                 135                 140

Leu Gly Phe Lys Ala Asp Thr Val Val Ala Ser Thr Trp Tyr Tyr Thr
145                 150                 155                 160

His Met Arg Asp Asn Thr Asn Ser Asn Gly Phe Phe Trp Asn Phe Ile
                165                 170                 175

Ser Glu Glu His Gly Trp Gln Glu Lys
                180                 185

<210> SEQ ID NO 7
<211> LENGTH: 194
<212> TYPE: PRT
<213> ORGANISM: Clostridium botulinum
<220> FEATURE:
<223> OTHER INFORMATION: Amino acids 1085 to 1278 of neurotoxin type F
<300> PUBLICATION INFORMATION:
<308> DATABASE ACCESSION NUMBER: VERSION CAA57358.1  GI:971349

<400> SEQUENCE: 7

Pro Asp Pro Ser Ile Leu Lys Asp Phe Trp Gly Asn Tyr Leu Leu Tyr
1                5                  10                  15

Asn Lys Arg Tyr Tyr Leu Leu Asn Leu Leu Arg Thr Asp Lys Ser Ile
                20                  25                  30

Thr Gln Asn Ser Asn Phe Leu Asn Ile Asn Gln Gln Arg Gly Val Tyr
            35                  40                  45

Gln Lys Pro Asn Ile Phe Ser Asn Thr Arg Leu Tyr Thr Gly Val Glu
        50                  55                  60

Val Ile Ile Arg Lys Asn Gly Ser Thr Asp Ile Ser Asn Thr Asp Asn
65                  70                  75                  80

Phe Val Arg Lys Asn Asp Leu Ala Tyr Ile Asn Val Val Asp Arg Asp
                85                  90                  95

Val Glu Tyr Arg Leu Tyr Ala Asp Ile Ser Ile Ala Lys Pro Glu Lys
            100                 105                 110

Ile Ile Lys Leu Ile Arg Thr Ser Asn Ser Asn Asn Ser Leu Gly Gln
        115                 120                 125

Ile Ile Val Met Asp Ser Ile Gly Asn Asn Cys Thr Met Asn Phe Gln
    130                 135                 140

Asn Asn Asn Gly Gly Asn Ile Gly Leu Leu Gly Phe His Ser Asn Asn
145                 150                 155                 160

Leu Val Ala Ser Ser Trp Tyr Tyr Asn Asn Ile Arg Lys Asn Thr Ser
                165                 170                 175

Ser Asn Gly Cys Phe Trp Ser Phe Ile Ser Lys Glu His Gly Trp Gln
            180                 185                 190

Glu Asn

<210> SEQ ID NO 8
<211> LENGTH: 193
<212> TYPE: PRT
<213> ORGANISM: Clostridium baratii
```

```
<220> FEATURE:
<223> OTHER INFORMATION: Amino acids 1076 to 1268 of neurotoxin type F
<300> PUBLICATION INFORMATION:
<308> DATABASE ACCESSION NUMBER: VERSION CAA48329.1  GI:49139

<400> SEQUENCE: 8

Pro Asp Ser Thr Ile Leu Lys Asp Phe Trp Gly Asn Tyr Leu Leu Tyr
1               5                  10                  15

Asn Lys Lys Tyr Tyr Leu Leu Asn Leu Leu Lys Pro Asn Met Ser Val
            20                  25                  30

Thr Lys Asn Ser Asp Ile Leu Asn Ile Asn Arg Gln Arg Gly Ile Tyr
        35                  40                  45

Ser Lys Thr Asn Ile Phe Ser Asn Ala Arg Leu Tyr Thr Gly Val Glu
    50                  55                  60

Val Ile Ile Arg Lys Val Gly Ser Thr Asp Thr Ser Asn Thr Asp Asn
65                  70                  75                  80

Phe Val Arg Lys Asn Asp Thr Val Tyr Ile Asn Val Val Asp Gly Asn
                85                  90                  95

Ser Glu Tyr Gln Leu Tyr Ala Asp Val Ser Thr Ser Ala Val Glu Lys
            100                 105                 110

Thr Ile Lys Leu Arg Arg Ile Ser Asn Ser Asn Tyr Asn Ser Asn Gln
        115                 120                 125

Met Ile Ile Met Asp Ser Ile Gly Asp Asn Cys Thr Met Asn Phe Lys
130                 135                 140

Thr Asn Asn Gly Asn Asp Ile Gly Leu Leu Gly Phe His Leu Asn Asn
145                 150                 155                 160

Leu Val Ala Ser Ser Trp Tyr Tyr Lys Asn Ile Arg Asn Asn Thr Arg
                165                 170                 175

Asn Asn Gly Cys Phe Trp Ser Phe Ile Ser Lys Glu His Gly Trp Gln
            180                 185                 190

Glu

<210> SEQ ID NO 9
<211> LENGTH: 211
<212> TYPE: PRT
<213> ORGANISM: Clostridium botulinum
<220> FEATURE:
<223> OTHER INFORMATION: Amino acids 1087 to 1297 of neurotoxin type G
<300> PUBLICATION INFORMATION:
<308> DATABASE ACCESSION NUMBER: VERSION CAA52275.1  GI:441276

<400> SEQUENCE: 9

Ser Ser Thr Asn Thr Leu Lys Asp Phe Trp Gly Asn Pro Leu Arg Tyr
1               5                  10                  15

Asp Thr Gln Tyr Tyr Leu Phe Asn Gln Gly Met Gln Asn Ile Tyr Ile
            20                  25                  30

Lys Tyr Phe Ser Lys Ala Ser Met Gly Glu Thr Ala Pro Arg Thr Asn
        35                  40                  45

Phe Asn Asn Ala Ala Ile Asn Tyr Gln Asn Leu Tyr Leu Gly Leu Arg
    50                  55                  60

Phe Ile Ile Lys Lys Ala Ser Asn Ser Arg Asn Ile Asn Asn Asp Asn
65                  70                  75                  80

Ile Val Arg Glu Gly Asp Tyr Ile Tyr Leu Asn Ile Asp Asn Ile Ser
                85                  90                  95

Asp Glu Ser Tyr Arg Val Tyr Val Leu Val Asn Ser Lys Glu Ile Gln
            100                 105                 110

Thr Gln Leu Phe Leu Ala Pro Ile Asn Asp Asp Pro Thr Phe Tyr Asp
        115                 120                 125
```

-continued

```
Val Leu Gln Ile Lys Lys Tyr Tyr Glu Lys Thr Thr Tyr Asn Cys Gln
    130                 135                 140

Ile Leu Cys Glu Lys Asp Thr Lys Thr Phe Gly Leu Phe Gly Ile Gly
145                 150                 155                 160

Lys Phe Val Lys Asp Tyr Gly Tyr Val Trp Asp Thr Tyr Asp Asn Tyr
                165                 170                 175

Phe Cys Ile Ser Gln Trp Tyr Leu Arg Arg Ile Ser Glu Asn Ile Asn
            180                 185                 190

Lys Leu Arg Leu Gly Cys Asn Trp Gln Phe Ile Pro Val Asp Glu Gly
        195                 200                 205

Trp Thr Glu
    210

<210> SEQ ID NO 10
<211> LENGTH: 426
<212> TYPE: PRT
<213> ORGANISM: Clostridium botulinum
<220> FEATURE:
<223> OTHER INFORMATION: Amino acids 866 to 1291 of neurotoxin type B
<300> PUBLICATION INFORMATION:
<308> DATABASE ACCESSION NUMBER: VERSION AAA23211.1  GI:144735

<400> SEQUENCE: 10

Leu Asn Leu Arg Tyr Lys Asp Asn Asn Leu Ile Asp Leu Ser Gly Tyr
1               5                   10                  15

Gly Ala Lys Val Glu Val Tyr Asp Gly Val Glu Leu Asn Asp Lys Asn
            20                  25                  30

Gln Phe Lys Leu Thr Ser Ser Ala Asn Ser Lys Ile Arg Val Thr Gln
        35                  40                  45

Asn Gln Asn Ile Ile Phe Asn Ser Val Phe Leu Asp Phe Ser Val Ser
    50                  55                  60

Phe Trp Ile Arg Ile Pro Lys Tyr Lys Asn Asp Gly Ile Gln Asn Tyr
65                  70                  75                  80

Ile His Asn Glu Tyr Thr Ile Ile Asn Cys Met Lys Asn Asn Ser Gly
                85                  90                  95

Trp Lys Ile Ser Ile Arg Gly Asn Arg Ile Ile Trp Thr Leu Ile Asp
            100                 105                 110

Ile Asn Gly Lys Thr Lys Ser Val Phe Phe Glu Tyr Asn Ile Arg Glu
        115                 120                 125

Asp Ile Ser Glu Tyr Ile Asn Arg Trp Phe Phe Val Thr Ile Thr Asn
    130                 135                 140

Asn Leu Asn Asn Ala Lys Ile Tyr Ile Asn Gly Lys Leu Glu Ser Asn
145                 150                 155                 160

Thr Asp Ile Lys Asp Ile Arg Glu Val Ile Ala Asn Gly Glu Ile Ile
                165                 170                 175

Phe Lys Leu Asp Gly Asp Ile Asp Arg Thr Gln Phe Ile Trp Met Lys
            180                 185                 190

Tyr Phe Ser Ile Phe Asn Thr Glu Leu Ser Gln Ser Asn Ile Glu Glu
        195                 200                 205

Arg Tyr Lys Ile Gln Ser Tyr Ser Glu Tyr Leu Lys Asp Phe Trp Gly
    210                 215                 220

Asn Pro Leu Met Tyr Asn Lys Glu Tyr Tyr Met Phe Asn Ala Gly Asn
225                 230                 235                 240

Lys Asn Ser Tyr Ile Lys Leu Lys Lys Asp Ser Pro Val Gly Glu Ile
                245                 250                 255

Leu Thr Arg Ser Lys Tyr Asn Gln Asn Ser Lys Tyr Ile Asn Tyr Arg
```

-continued

```
                    260                 265                 270
Asp Leu Tyr Ile Gly Glu Lys Phe Ile Ile Arg Arg Lys Ser Asn Ser
                275                 280                 285

Gln Ser Ile Asn Asp Asp Ile Val Arg Lys Glu Asp Tyr Ile Tyr Leu
            290                 295                 300

Asp Phe Phe Asn Leu Asn Gln Glu Trp Arg Val Tyr Thr Tyr Lys Tyr
305                 310                 315                 320

Phe Lys Lys Glu Glu Lys Leu Phe Leu Ala Pro Ile Ser Asp Ser
                325                 330                 335

Asp Glu Phe Tyr Asn Thr Ile Gln Ile Lys Glu Tyr Asp Glu Gln Pro
                340                 345                 350

Thr Tyr Ser Cys Gln Leu Leu Phe Lys Lys Asp Glu Glu Ser Thr Asp
                355                 360                 365

Glu Ile Gly Leu Ile Gly Ile His Arg Phe Tyr Glu Ser Gly Ile Val
                370                 375                 380

Phe Glu Glu Tyr Lys Asp Tyr Phe Cys Ile Ser Lys Trp Tyr Leu Lys
385                 390                 395                 400

Glu Val Lys Arg Lys Pro Tyr Asn Leu Lys Leu Gly Cys Asn Trp Gln
                405                 410                 415

Phe Ile Pro Lys Asp Glu Gly Trp Thr Glu
                420                 425

<210> SEQ ID NO 11
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: MOD_RES
<222> LOCATION: (6)..(40)
<223> OTHER INFORMATION: Any amino acid; this region may encompass 33-35
      residues
<220> FEATURE:
<221> NAME/KEY: MOD_RES
<222> LOCATION: (42)..(131)
<223> OTHER INFORMATION: Any amino acid; this region may encompass 84-90
      residues
<220> FEATURE:
<221> NAME/KEY: MOD_RES
<222> LOCATION: (133)..(143)
<223> OTHER INFORMATION: Any amino acid
<220> FEATURE:
<221> NAME/KEY: MOD_RES
<222> LOCATION: (145)..(146)
<223> OTHER INFORMATION: Any amino acid

<400> SEQUENCE: 11

His Glu Leu Xaa His Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Glu Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80
```

```
Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Glu Xaa Xaa Xaa Xaa Xaa Xaa Xaa Xaa Xaa Xaa Arg
    130                 135                 140

Xaa Xaa Tyr
145

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      6xHN tag

<400> SEQUENCE: 12

His Asn His Asn His Asn His Asn His Asn His Asn
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 13

His His His His His His
1               5
```

TRANSPORT PROTEIN WHICH IS USED TO INTRODUCE CHEMICAL COMPOUNDS INTO NERVE CELLS

RELATED APPLICATIONS

This application is the U.S. National Stage of International Application No. PCT/EP2005/009554, filed Sep. 6, 2005, published in German, and claims priority under 35 U.S.C. §119 or 365 to German Application No. 10 2004 043 009.8, filed Sep. 6, 2004.

SEQUENCE LISTING

The instant application contains a Sequence Listing which has been submitted in ASCII format via EFS-Web and is hereby incorporated by reference in its entirety.

The present invention relates to a transport protein which binds to neurons, is accommodated by receptor-mediated endocytosis and is translocated from the acid, endosomal compartment into the cytosol of neurons. This protein is used as a transporting means for translocating other chemical substances (e.g. proteases), which are unable physiologically to penetrate into the cytosol of nerve cells through the plasma membrane. The present invention relates to the use of a transport protein for inhibiting the release of neurotransmitters.

Nerve cells release transmitter substances by exocytosis. The fusion of the membranes of intracellular vesicles with the plasma membrane is referred to as exocytosis. In the course of this process the vesicular contents is simultaneously discharged into the synaptic gap. The fusion of the two membranes is regulated by calcium, reacting with the protein synaptotagmin. Together with other co-factors synaptotagmin controls the status of three so-called fusion proteins, SNAP-25, synaptobrevin 2 and syntaxin 1A. While syntaxin 1A and synaptobrevin 2 are integrated into the plasma and/or vesicle membrane, SNAP-25 binds only lightly to the plasma membrane. To the extent that the intracellular calcium concentration increases, the three proteins bind to one another, both membranes approaching one another and subsequently fusing together. In the case of cholinergic neurons acetyl choline is released, causing muscle contractions, perspiration and other cholinergically provoked reactions.

The above mentioned fusion proteins are the target molecules (substrates) of the light chains of the clostridial neurotoxins, formed by the bacterium *Clostridium botulinum*.

The anaerobic, gram-positive bacterium *Clostridium botulinum* produces seven different types of protein neurotoxins. The latter are referred to as the Botulinus neurotoxins (BoNT/A to BoNT/G). Among these, in particular BoNT/A and BoNT/B cause a neuroparalytic disorder in humans and animals, referred to as botulism. The spores of *Clostridium botulinum* can be found in the soil, but may also develop in incorrectly sterilised and sealed home-made food preserves, to which many cases of botulism are attributed.

BoNT/A is the most lethal of all known biological substances. As little as 5-6 pg of purified BoNT/A represents an MLD (Multiple Low Dose). One unit (Engl.: Unit, U) of BONT is defined as the MLD, killing half of the female Swiss Webster mice, each weighing 18-20 g, after intraperitoneal injection. Seven immunologically different BoNTs were characterised. They are denoted as BoNT/A, B, $C_1$, D, E, F and G and may be distinguished by neutralisation with serotype-specific antibodies. The different serotypes of BoNTs differ in affected animal species with regard to severity and duration of the paralysis caused. Thus, with regard to paralysis, BoNT/A is 500 times more potent in rats for example, than BoNT/B. In addition, BoNT/B has proved to be non-toxic in primates at a dosage of 480 U/kg of body weight. The same quantity of BoNT/A corresponds to 12 times the lethal dose (LD) of this substance in primates. On the other hand, the duration of paralysis after BoNT/A injection in mice is ten times longer than after injection of BoNT/E.

BoNTs have been used clinically for treating neuromuscular disorders, characterised by hyperactivity in skeleton muscles, caused by pathologically overactive peripheral nerves. BoNT/A has been approved by the U.S. Food and Drug Administration for treating blepharo-spasm, strabism and hemi-facial spasms. Compared with BoNT/A the remaining BONT serotypes are evidently less efficacious and manifest a shorter duration of efficacy. Clinical effects of BoNT/A administered peripheral-intramuscularly are usually noticeable within a week. The duration of symptom suppression by one single intramuscular injection of BoNT/A is normally about 3 months.

The clostridial neurotoxins specifically hydrolyse different proteins of the fusion apparatus. BoNT/A, $C_1$ and E split SNAP-25, while BoNT/B, D, F, G as well as tetanus neurotoxin (TeNT) attack the vesicle-associated membrane protein (VAMP) 2-also referred to as synaptobrevin 2-BoNT/$C_1$ furthermore splits syntaxin 1A.

The *Clostridium* bacteria release the neurotoxins as single-chain polypeptides each having 1251 to 1315 amino acids. Thereafter endogenous proteases split each of these proteins at a defined location into 2 chains each ('nicking'), the two chains however remaining interlinked by a disulphide-bridge. These dual-chain proteins are referred to as holo-toxins (see Shone et al. (1985), Eur J Biochem 151, 75-82). The two chains have different functions. While the smaller fragment, the light chain (light chain=LC), represents a $Zn^{2+}$-dependent endoprotease, the larger unit (heavy chain=HC) represents the transporting means of the light chain. By treating the HC with endopeptidases two 50 kDa fragments were brought about (see Gimenez et al. (1993), J Protein Chem 12, 351-363). The amino-terminal half ($H_N$-fragment) integrates into membranes at a low pH-value and enables the LC to penetrate into the cytosol of the nerve cell. The carboxy-terminal half ($H_C$-fragment) binds to complex polysialogangliosides, occurring exclusively in nerve cell membranes and to protein receptors not identified to date (Halpern et al. (1993), Curr Top Microbial Immunol 195, 221-241). The latter explains the high neuroselectivity of the clostridial neurotoxins. Crystalline structures confirm that BoNT/A disposes of three domains, which may be harmonised by the three steps of the action mechanism (see Lacy et al. (1998), Nat Struct Biol 5, 898-902). Moreover, these data give rise to the conclusion that within the $H_C$-fragment two autonomous subunits (sub-domains) exist of 25 kDa each. The first proof for the existence of the two functional sub-domains was brought about by the amino-terminal ($H_{CN}$ and the carboxy-terminal half ($H_{CC}$) of the $H_C$-fragment of the TeNT, which were expressed in recombinant form and which revealed that the $H_{CC}$-, but not the $H_{CN}$ domain binds to neurons (see Herreros et al. (2000), Biochem J 347, 199-204). The protein receptor-binding site of the synaptotagmin was discovered inside the $H_{CC}$-domains of BoNT/B and G, proving their separate functionality (see Rummel et al. (2004), J Biol Chem 279, 30865-70).

Under physiological conditions the HC binds to neuronal gangliosides, is received inside the cell by receptor-mediated endocytosis and reaches the natural vesicle circulation via the endosomal compartment. In the acid medium of the early endosomes, $H_N$, the amino-terminal half of HC, penetrates into the vesicle membrane and forms a pore. Each substance (X), linked to HC via a disulphide bridge, will be split off the HC by intracellular redox systems, gaining access to the disulphide bridge and reducing it. X will ultimately appear in the cytosol.

In the case of the clostridial neurotoxins the HC is the carrier of an LC, splitting its specific substrate in the cytosol in the final step. The cycle of complex formation and dissociation of the fusion proteins is interrupted and the release of acetyl choline is consequently inhibited. As a result thereof, striated muscles are paralysed and sweat glands cease their secretion. The active period of the individual BoNT serotypes differs and depends on the presence of intact LC in the cytosol. As all neurons possess receptors for clostridial neurotoxins, it is not only the release of acetyl choline which may be affected, but potentially also the release of the substance P, of noradrenalin, GABA, glycine, endorphin and other transmitters and hormones.

That the cholinergic transmission is blocked preferentially, may be explained by the fact that the HC in the periphery enters into the neuron. Central synapses are protected by the blood-brain-barrier, which cannot be surmounted by proteins.

The HCs possess a high affinity for peripheral nerve cells, mediated predominantly by the interaction with complex polysialogangliosides—these are glycol lipids composed of more than one sialine acid (see Halpern et al. (1995), Curr Top Microbiol Immunol 195, 221-41). As a result, the LCs binding to them reach only this cell type and become active only in these cells. BoNT/A and B bind merely one molecule ganglioside GT1b each.

In order to research the role played by the amino acids, which build the binding pocket, a recombinant $H_C$-fragment was produced according to the invention. This technique permits to exchange individual amino acids. Thus, positively-charged amino acids may be substituted by negatively-charged or neutral amino acids, and vice versa. Slight modifications in the surface of the binding pocket produce no dramatic effect regarding the passing ability of the gangliosides. It could be shown that the affinity receded by more than 99%, if e.g. the amino acid in position 1266, the tryptophane—referred to as W in the SXWY-motive—is substituted by an aliphatic residue, e.g. leucine. However, the contrary has also been observed. The substitution of amino acids, extending into the binding pocket, resulted in an increase of the affinity to gangliosides. Since the configuration of the binding pocket is so decisive for the affinity of the HC to the ganglioside receptor, the proteolytic potency of the associated LC, simultaneously with the affinity of the HC to the ganglioside receptor, either increases or decreases in harmony with the affinity.

In a ligand-receptor-study specific amino acid residues were thus characterised according to the invention in the ganglioside-binding pocket of BoNT/A and substituted in order to increase the affinity to the ganglioside receptor accordingly. The affinity of the mutated $H_C$-fragment was determined in ganglioside and synaptosome-binding assays. Subsequently, the HC exhibiting the same mutations was coupled to LC-A, for which purpose a thrombin-sensitive amino acid sequence was used. The recombinant protein was activated ('nicked') by thrombin and resulted in a double-chain molecule, both chains being interlinked by a single disulphide bridge. The activity of the constructs was tested in synaptosomes of rat brain—a preparation releasing transmitters. The extent of transmitter release inhibition was considered as the measure of the degree of activity of the constructs. In addition, the potency of the individual constructs was analysed by means of the isolated nerve-muscle-preparation of the mouse (Hemi-Diaphragma-Assay=HDA), representing the physiological object of clostridial neurotoxins.

Disorders and symptoms which are to be treated with TrapoX are accompanied by a focally increased activity of motor neurons and vegetative nerve cells. The increased activity results in painful cramps of the muscles innerved by these cells and in an excessive liquid secretion from gland cells. Furthermore, facial wrinkles occur in different regions due to the increased activity. The cause is a pathologically increased release of acetyl choline from the peripheral nerve ends. If TrapoX is injected into the affected muscle, a relaxation of the affected muscles, the drying up of secretion and smoothing of the facial skin comes about after a latency of 1-3 days. This is due to an inhibition of the release of acetyl choline by TrapoX. The patient becomes virtually pain-free and the pain provoked by the muscle cramp is alleviated and disappears completely.

The release of acetyl choline is inhibited both in humans as well as in animals. Animal testing is therefore used routinely both as evidence of BoNT in poisoning cases as well as for activity determination of BoNT-drugs (Botox, Dysport, Xeomin). The activity of BoNT is quantified by performing a determination of the $LD_{50}$ in mice. In this context one determines the dose, killing 50% of the animals of one test group. It is obvious that apart from doses not destroying any animal, doses may be administered killing 100% of the animals from one group. Since the poison is administered systemically (i.p.), a large number of animals thus die painfully of respiratory arrest, caused by a paralysis of the respiratory muscles. In order to avoid animal tests, we have introduced the Mouse Hemi-Diaphragma Assay. With the $LD_{50}$ test, trial mice die of respiratory paralysis, caused by paralysis of the respiratory muscles. This means that the respiratory muscle, including the innerving nerve (*Nervus phrenicus*) can be removed from the mouse and be poisoned in vitro. BoNT will bind to its receptors, will enter the cell and be translocated and will finally split its substrate, whereupon the muscle paralyses. There is a strict correlation between the $LD_{50}$ value and the paralysis of the respiratory muscle. This in vitro test represents, as it were, a watered-down version of the animal test (Wohtfarth K, Goeschel H, Frevert J, Dengler R, Bigalke H, Botolinum A toxis: units versus units. Naunyn Schmiedeberg's Arch Pharmacol. 1997 Mar; 335(3):335-40).

One can therefore assume that the BoNT, paralysing the diaphragm in vitro, also acts in the living mouse, killing the latter according to the dose administered. This animal test replacement method is so convincing that the Mouse Hemi-Diaphragma-Assay will shortly be accepted for the EU member states by the EU Pharmacopoeia as the official testing method for BoNT. The increased efficacy of TrapoX in the mouse diaphragm preparation thus suggests an increased efficacy in humans as well.

In the more recent past, the BoNT/A complex was used for treating motor dystonias, as well as for attenuating excessive sympathetic activity (see Benecke et al. (1995), Akt Neurol 22, 209ff) and for alleviating pain and migraine (see Sycha et al. (2004), J Neurol 251,19-30). This complex consists of the neurotoxin, various haemagglutinines and a non-toxic, non-haemagglutinating protein. The complex dissociates rapidly at physiological pH. The resultant neurotoxin is the sole ingredient of the complex which is therapeutically relevant and brings about an alleviation of the symptoms. Since the underlying neurological illness is not cured, the complex needs to be injected again at intervals of three to four months. Depending on the quantity of the injected foreign protein, some patients develop specific BoNT/A-antibodies. These patients become resistant to the neurotoxin. Once antigensensitive cells have recognised the neurotoxin and antibodies have been formed, the relevant brain cells are conserved over years. For this reason it is important to treat the patient with preparations of the highest possible activity at the lowest possible dosage. The preparations should furthermore not contain any further proteins of bacterial origin, since these may act as immuno-adjuvants. Such substances attract macrophages, which recognise both the immuno-adjuvants as well as the neurotoxins, presenting them to the lymphocytes, which thereupon respond by forming immunoglobulins. Consequently, only products of extreme purity, not containing any foreign proteins, may be used for therapy.

The present invention now provides a transport protein (Trapo), which is able to overcome the above described problems of the methods known to date.

Preferably, a transport protein (Trapo) is provided, the affinity of which to complex gangliosides is increased at least three fold.

"Binding to nerve cells with a higher affinity than native neurotoxin". The native neurotoxin is in this case preferably the native neurotoxin of *C. botulinum*. Preferably, the native neurotoxin is in this context Botulinus neurotoxin A and/or Botulinus neurotoxin B and/or Botulinus neurotoxin G from *C. botulinum*. The Botulinus neurotoxin prepared in recombinant form from *E. coli*, which, inter alia, contains the amino acid sequence identical to the native Botulinus neurotoxin, acts in a pharmacologically identical manner to the native Botulinus neurotoxin and is referred to as recombinant Botulinus neurotoxin wild type. The nerve cells mentioned in this case are cholinergic motor neurons. Preferably, the transport protein binds specifically to polysialogangliosides on the nerve cell membrane surface, such as e.g. GD1a, GD1b or GT1b. The binding is determined preferably in vitro. Particularly preferably, the determination is performed by the use of an assay, elucidated in detail in the examples.

The term "modification of the heavy chain of the neurotoxin formed by *C. Botulinum*." The amino acid and/or nucleic acid sequence of the heavy chain (HC) of the neurotoxin formed by *C. botulinum* are generally available from publicly accessible databases, for each of the known serotypes A to G (also refer to table 1). Modification includes in this context that at least one amino acid is deleted, added, is inserted into the amino acid sequence, or that at least one amino acid of the native neurotoxin is substituted by another naturally occurring or not naturally occurring amino acid and/or that one amino acid in the stated amino acid sequence is modified post-translationally. Post-translational modifications include in this context glycosylations, acetylations, acylations, de-aminations, phosphorylisations, isoprenylisations, glycosyl phosphatidyl inositolisations and further modifications known to the person skilled in the art.

The HC of the neurotoxin formed by *C. botulinum* includes three sub-domains, i.e. the amino-terminal 50 kDa-sized translocation domain $H_N$, the 25 kDa HCN-domain following thereon, and the carboxyl-terminally situated 25 kDa $H_{CC}$-domain. Together, the $H_{CN}$- and $H_{CC}$-domains are denoted as $H_C$-fragment. The corresponding amino acid sections of the respective sub-domains for the individual serotypes and their variations are apparent from Table 1.

In order to describe in detail hybrid proteins with domains of different BoNT serotypes, the following nomenclature is introduced in what follows. The term scAtAAB denotes e.g. a single-chain neurotoxin (sc), consisting of the four domains LC, $H_N$, $H_{CN}$ and $H_{CC}$, each domain, according to its origin, being marked by the capital letter of the respective serotype. This means that scAtAAB is derived from LC, $H_N$ and $H_{CN}$, while the Hcc-domain of BoNT/A was substituted by BoNT/

B. The small letter "t" symbolises an inserted thrombin marker sequence between LC and $H_N$.

TABLE 1

Database numbers of the amino acid sequences and distribution of the sub-domains of the seven Botulinus neurotoxins.

| BoNT | Database no. of the protein sequence | Number of the amino acids | $H_N$ | HC $H_{CN}$ | $H_C$ $H_{CC}$ |
|---|---|---|---|---|---|
| BoNT/A | AAA23262 AAM75961 AAQ06331 BTCLAB | 1296 | 449-866 | 867-1091 | 1092-1296 |
|  | P10845 | 1296 | 449-866 | 867-1091 | 1092-1296 |
|  | CAA36289 | 1296 | 449-866 | 867-1091 | 1092-1296 |
|  | CAA51824 I40645 Q45894 | 1296 | 449-866 | 867-1091 | 1092-1296 |
| BoNT/B | AAL11499 AAL11498 |  |  |  |  |
|  | CAA73968 | 1291 | 442-855 | 866-1078 | 1079-1291 |
|  | AAK97132 | 1291 | 442-855 | 866-1078 | 1079-1291 |
|  | A48940 AAA23211 P10844 | 1291 | 442-855 | 866-1078 | 1079-1291 |
|  | BAC22064 | 1291 | 442-855 | 866-1078 | 1079-1291 |
|  | CAA50482 I40631 | 1291 | 442-855 | 866-1078 | 1079-1291 |
| BoNT/C1 | A49777 BAA14235 BAB71749 CAA51313 S46431 | 1291 | 450-863 | 864-1092 | 1093-1291 |
|  | P18640 | 1291 | 450-863 | 864-1092 | 1093-1291 |
|  | BAA08418 | 1280 | 450-863 | 864-1083 | 1084-1280 |
|  | BAA89713 | 1280 | 450-863 | 864-1083 | 1084-1280 |
| BoNT/D | CAA38175 P19321 S11455 | 1276 | 446-859 | 860-1079 | 1080-1276 |
|  | AAB24244 | 1276 | 446-859 | 860-1079 | 1080-1276 |
|  | BAA07477 S70582 | 1285 | 446-859 | 860-1088 | 1089-1285 |
|  | BAA90661 | 1285 | 446-859 | 860-1088 | 1089-1285 |
| BoNT/E | BAB86845 CAA44558 S21178 | 1252 | 423-842 | 843-1066 | 1067-1252 |
|  | CAA43999 Q00496 | 1251 | 423-842 | 843-1066 | 1067-1251 |
|  | CAA43998 JH0256 P30995 | 1251 | 423-842 | 843-1066 | 1067-1251 |
| BoNT/F | 1904210A AAA23263 I40813 P30996 | 1274 | 440-860 | 861-1086 | 1087-1274 |
|  | CAA73972 | 1280 | 440-861 | 862-1087 | 1088-1280 |
|  | AAA23210 CAA57358 | 1278 | 440-861 | 862-1084 | 1085-1278 |
|  | CAA48329 S33411 | 1268 | 432-853 | 854-1075 | 1076-1268 |
| BoNT/G | CAA52275 Q60393 S39791 | 1297 | 447-860 | 861-1086 | 1087-1297 |

The present invention relates, in particular, to a transport protein, obtained by modifying the HC of the neurotoxin formed by *Clostridium botulinum*, the said protein, with a higher affinity than the native neurotoxin, binding specifically to nerve cells and being received by these cells by endocytosis.

The transport protein provided in the present invention exhibits an increased specific affinity of its ganglioside-binding domain to complex polysialogangliosides. The increase of the affinity is preferably attained by substitution or deletion of amino acids.

According to a preferred embodiment the transport protein exhibits an affinity which is at least 15% higher than the native neurotoxin. Preferably, the transport protein exhibits an affinity which is at least 50% higher, particularly preferably at least 80% higher and in particular at least 90% higher than the native neurotoxin.

According to a preferred embodiment the modification of the HC takes place in the region of the $H_C$-fragment of the given neurotoxin. If the modification includes a substitution, deletion, insertion or addition, the latter may also be performed, for example, by specific mutagenesis, methods in this context being known to the person skilled in the art. The amino acids present in the native neurotoxin are in this context modified either by naturally occurring or by not naturally occurring amino acids. Amino acids are, in principle, divided into different physicochemical groups. Aspartate and glutamate belong to the negatively-charged amino acids. Histidine, arginine and lysine belong to the positively-charged amino acids. Asparagine, glutamine, serine, threonine, cysteine and tyrosine belong to the polar amino acids. Glycine, alanine, valine, leucine, isoleucine, methionine, proline, phenylalanine and tryptophane belong to the non polar amino acids. Aromatic side groups are to be found among the amino acids histidine, phenylatanine, tyrosine and tryptophane. In general, it is preferred to substitute an amino acid by a different amino acid pertaining to another physicochemical group.

According to a preferred embodiment of the invention, the transport protein is a Botulinus neurotoxin serotype A to G.

In a preferred embodiment of the invention, the transport protein is derived from the protein sequence of the *Clostridium botulinum* neurotoxin type A (database no. AAA23262 (SEQ ID NO: 1) and CAA51824).

A further embodiment of the present invention relates to a transport protein, wherein at least one amino acid in the positions 1117, 1202 to 1204, 1252 to 1254, 1262 to 1267, 1270 and 1278 to 1279 of the protein sequence of the *Clostridium botulinum* neurotoxin type A (database no. AAA23262 and CAA51824) has either been removed or been substituted by a naturally occurring or not naturally occurring amino acid.

A further embodiment of the present invention relates to a transport protein, wherein amino acids in positions 1092 to 1296 of the protein sequence of the *Clostridium botulinum* neurotoxin type A (database no. AAA23262 and CAA51824)—a region including the ganglioside-binding Domain—have been substituted by the sequence of *Clostridium botulinum* neurotoxin type B protein (database no. AAA23211), amino acids 1079 to 1291 (SEQ ID NO: 2),

*Clostridium botulinum* neurotoxin type $C_1$ protein (database no. CAA51313), amino acids 1093 to 1291 (SEQ ID NO: 3),

*Clostridium botulinum* neurotoxin type D protein (database no. CAA38175), amino acids 1080 to 1276 (SEQ ID NO: 4),

*Clostridium botulinum* neurotoxin type E protein (database no. CAA44558), amino acids 1067 to 1252 (SEQ ID NO: 5),

*Clostridium butyricum* neurotoxin type E protein (database no. CAA43998), amino acids 1067 to 1251 (SEQ ID NO: 6),

*Clostridium botulinum* neurotoxin type F protein (database no. CAA57358), amino acids 1085 to 1278 (SEQ ID NO: 7),

*Clostridium baratii* neurotoxin type F protein (database no. CAA48329), amino acids 1076 to 1268 (SEQ ID NO: 8),

*Clostridium botulinum* neurotoxin type G protein (database no. CAA52275), amino acids 1087 to 1297 (SEQ ID NO: 9).

Further $H_{CC}$-domains suitable for interchangeability with amino acid positions are apparent from Table 1.

A further embodiment of the present invention relates to a composition containing a transport protein according to the invention and at least one intervening molecule (X). The intervening molecule may be a small organic molecule, a peptide or a protein; preferably covalently bonded, e.g. by a peptide-, ester-, ether-, sulphide-, disulphide- or carbon-carbon-bond.

In addition, the intervening molecule includes all known therapeutically active substances. Cytostatics, antibiotics, virustatics, but also immunoglobulins are preferred in this context.

In order to better utilise the increased affinity of the Trapo, it was bound amino-terminally to an LC of BoNT/A, B, $C_1$, D, E, F or G via an amino acid sequence, which is specifically recognised and split by the protease thrombin, bringing about a specific TrapoX. The active strength of the said TrapoX, in comparison with native BoNT/A, was increased and particularly preferred by a factor of at least 3. This new product, which is free of foreign proteins, will dramatically reduce the stimulation of the immune systems due to the greater purity of the material and the low dosage.

A further embodiment of the present invention relates to a transport protein, wherein the protein is a protease, splitting one or a plurality of proteins of the release apparatus of neurotransmitters, the protease being selected from the group of neurotoxins consisting of the LC of the *Clostridium botulinum* neurotoxins, in particular of type A, B, $C_1$, D, E, F and G or a proteolytically active fragment of the LC of a *Clostridium botulinum* neurotoxin, in particular a neurotoxin of serotype A, B, $C_1$, D, E, F and G, the fragment exhibiting at least 0,01% of the proteolytic activity of the native protease, preferably at least 5%, particularly preferably at least 50%, in particular at least 90%. Preferably, the transport protein and the protease are derived from the same *C. botulinum* neurotoxin serotype, in particular and preferably the $H_N$-domain of the transport protein and the protease are derived from the *C. botulinum* neurotoxin serotype A. The sequences of the proteases are generally accessible at databases and the database numbers are apparent from Table 1. The proteolytic activity of the proteases is determined by way of substrate separation kinetics (see Bina et al. (2002), Biochemistry 41(6), 1717-23).

The LCs are characterised in that they contain the sequence His-Glu-Leu-Xaa-His-$(Xaa)_{33-35}$-Glu$(Xaa)_{84-90}$-Glu-(Xaa)$_{11}$-Arg-Xaa-Xaa-Tyr (SEQ ID NO: 11), wherein Xaa may be any amino acid. The transport protein of the present invention is characterised in that the protein and the protease stem from the previous groups of proteins and/or proteases.

According to a further embodiment of the present invention, a method for producing the transport protein is provided. In this case, in a first step a nucleic acid coding for the transport protein is provided. The coding nucleic acid may represent in this context RNA, DNA or mixtures thereof. The nucleic acid may furthermore be modified with regard to its nuclease resistance, such as e.g. by inserting phosphorthioate bonds. The nucleic acid may be produced from a starting nucleic acid, the latter being accessible e.g. by cloning from genomic or cDNA-databases. Moreover, the nucleic acid may be produced directly by solid phase synthesis. Suitable methods are known to the person skilled in the art. If one assumes a starting nucleic acid, a specific modification, e.g. by locality-specific mutagenesis, may be brought about, resulting in at least one addition, insertion, deletion and/or substitution on the amino acid level. The nucleic acid is then linked operatively to a suitable promoter. Suitable promoters for expression in known expression systems are known to the person skilled in the art. The choice of promoter depends in this case on the expression systems used for expression. In general, constitutive promoters are preferred, but inducible promoters may likewise be used. The construct produced in this manner includes at least one part of a vector, in particular regulatory elements, the vector, for example, being selected from λ-derivates, adenoviruses, baculoviruses, vaccinia viruses, SV40-viruses and retroviruses. The vector is preferably capable of expressing the nucleic acid in a given host cell.

The invention further provides host cells, which contain the vector and are suitable for expressing the vector. Numerous prokaryotic and eukaryotic expression systems are known in the state of the art, the host cells being selected, for example, from prokaryotic cells such as *E. coli* or *B. megaterium*, from eukaryotic cells such as *S. cerevisiae* and *P. pastoris*. Although higher eukaryotic cells, such as insect cells or mammal cells, may be used as well, host cells are nevertheless preferred, which, like *C. botulinum*, do not possess a glycosylation apparatus.

According to a preferred embodiment the nucleic acid codes for the $H_{CC}$-domain of the *C. botulinum* neurotoxin. This nucleic acid contains endonuclease-interfaces, flanking the nucleic acid coding for the $H_C$-fragment, the endonuclease sites being compatible with those of other $H_C$-fragments of *C. botulinum* neurotoxins, in order to permit their easy modular substitution in the gene coding for the transport protein, while the similarity of the amino acid sequence is preserved.

If a composition according to the invention is provided, which, apart from the transport system, further contains at least one intervening molecule, and this intervening molecule, a peptide or protein, is functionalised either with a carboxy-terminal cysteine or a mercapto-group, then, in an analogous manner, as described before, the peptide and/or protein may be produced recombinantly, for example by using binary vectors or various host cells. If the same host cell is used for the expression both of the transport protein and the peptide or protein, an intermolecular disulphide bond is preferably formed in situ. For a more efficient production in the same host cell, the nucleic acid coding for the peptide or protein may also be translated with that of the transport protein in the same reading frame, so that a single-chain polypeptide is produced. In this case preferably an intramblecular disulphide bond is formed in situ. For simple hydrolysis of the likewise present peptide cross-linking between the transport protein and the peptide and/or protein, an amino acid sequence is inserted at the amino-terminus of the transport protein, which is either specifically recognised and separated by the protease thrombin or by a specific endoprotease of the host cell.

If this is not possible, an appropriate intermolecular disulphide-linkage, after separate purification of the transport protein and the protein, may subsequently be brought about by oxidation processes known to the person skilled in the art. The peptide or protein may also be obtained directly by synthesis or fragment condensation. Appropriate methods are known to the person skilled in the art.

The transport protein and the peptide, or protein respectively, are subsequently purified. For this purpose methods are used, known to the person skilled in the art, such as e.g. chromatography-methods or electrophoresis.

A further embodiment of the present invention relates to the pharmaceutical composition, including the transport protein and optionally a pharmaceutically acceptable excipient, a diluent and/or an additive and Which is suitable to treat the following disorders or diseases: hemi-facial spasms, spasmodic torticollis, spasticities, dystonias, migraine, pain, disorders of the neck and lumbar vertebral column, strabism, hypersalivation and depressive diseases.

The pharmaceutical composition is suitable for oral, intravenous, subcutaneous, intramuscular and topical administration. Intramuscular administration is preferred. A dosing unit of the pharmaceutical composition contains approximately 0,1 pg to 1 mg of transport protein and/or the composition according to the invention.

A further embodiment of the present invention includes a cosmetic composition, consisting of the transport protein and a pharmaceutical excipient, a diluent and/or an additive, suitable for treating hyperhydrosis and very pronounced facial wrinkles. The cosmetic composition is suitable for oral, intravenous, subcutaneous, intramuscular and topical administration. Intramuscular administration is preferred. A dosing unit of the cosmetic composition contains about 0,1 pg to 1 mg of transport protein and/or the composition according to the invention. The cosmetic composition is suitable to treat hyperhydrosis and facial wrinkles.

The transport protein described in the present invention may be produced by a suitable host cell, such as e.g. *Escherichia coli*, *Saccharomyces cerevisiae*, *Pichia pastoris* or *Bacillus megaterium*, which multiplies a recombinant expression vector, the vector coding for a transport protein.

The present invention is elucidated by the accompanying drawings, wherein:

FIG. 1 shows that the affinity of the mutated $H_C$-fragment of BoNT/A to synaptosome membrane preparations from the rat brain is three times higher than that of the $H_C$-fragment of the wild type of BoNT/A.

FIG. 2 shows the binding of different BoNT/A $H_C$-fragment mutants to rat brain synaptosomes, the affinity of the BoNT/A $H_C$-fragment wild type being set to 100% as a standard. The first column shows the affinities of the BoNT/A mutants, showing mutations of the amino acids Y1117 resulting in an increase. The second column shows further BoNT/A-mutants. The third column shows the affinities of BoNT/A-mutants exhibiting double mutations, which enhance the binding to nerve cell membranes (synaptosomes).

FIG. 3 shows the increased neurotoxicity of the Y1117A-mutant of BoNT/A in comparison with the BoNT/A-wild type on the isolated *nervus phrenicus—diaphragm muscle-preparation of the mouse*.

FIG. 4 shows the binding of the four BoNT/A $H_C$-fragment hybrids $H_CAB$, $H_CAC$, $H_CAE$ and $H_CAT$ (T=tetanus neurotoxin) in nerve cell membranes (synaptosomes), the BoNT/A $H_C$-fragment wild type being set to 100% as a standard.

Figure 5:
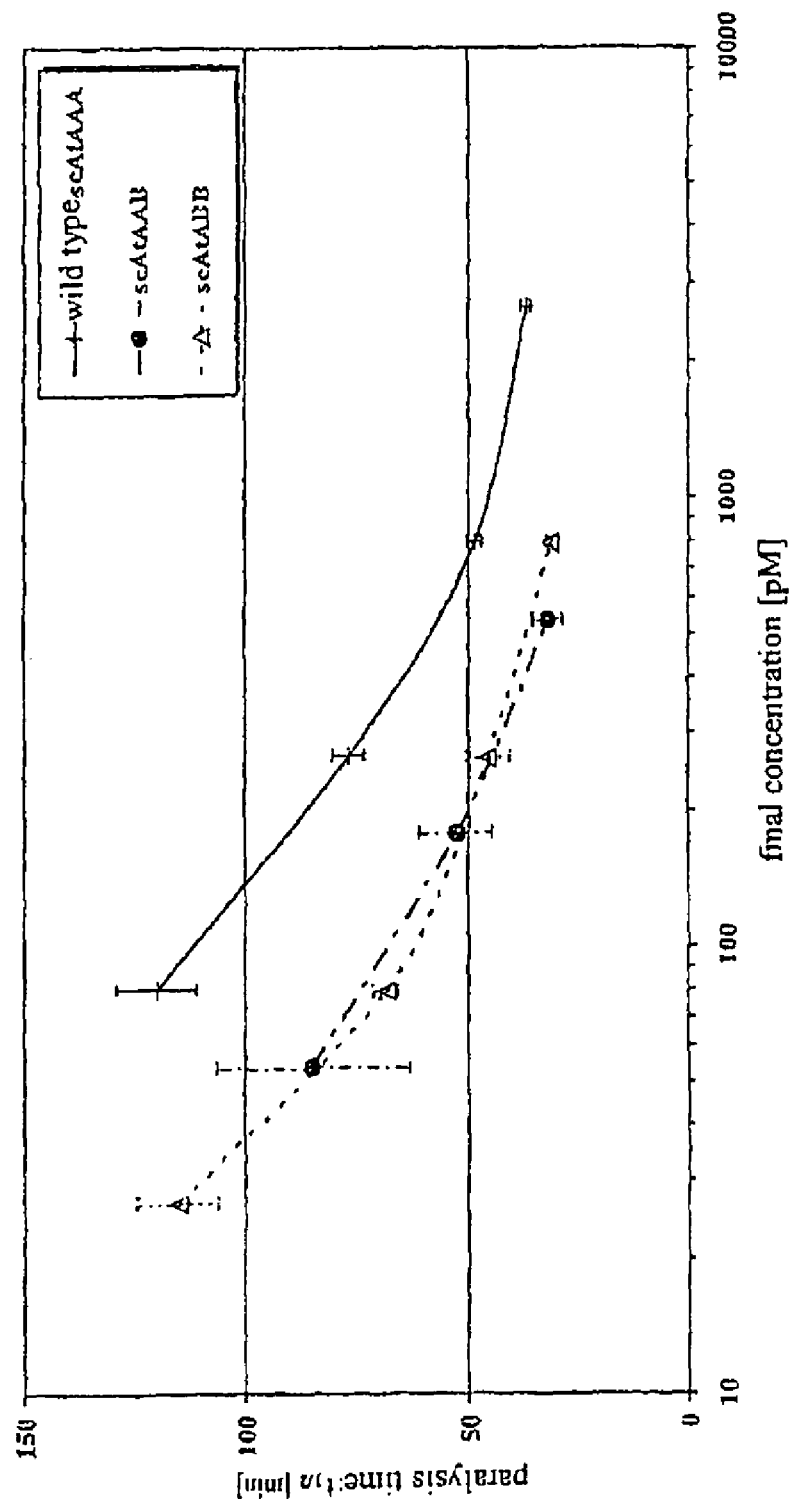
FIG. 5 shows the increased neurotoxicity of the total toxin hybrids consisting of BoNT/A and either the $H_C$-fragment or the $H_{CC}$-domain of BoNT/B in comparison with the BoNT/A-wild type in the isolated *nervus phrenicus*—diaphragm muscle-preparation of the mouse.

In detail, the present invention contains a transport protein (Trapo), formed by a modification of the HC of the neurotoxin produced by *Clostridium botulinum*, preferably specifically binding to neurons, accommodated intracellularly by receptor-mediated endocytosis and translocated from the acid endosomal compartment into the cytosol of neurons. This protein is used as a transporting means in order to introduce into the cells proteases and other substances bound to the said transporting means, unable to penetrate physiologically into the plasma membrane and to reach the cytosol of nerve cells. The substrates of the proteases are intracellularly localised proteins and peptides participating in the transmitter release. After separation of the substrates, the specific functions of the neurons are blocked; the cells themselves are not damaged. One of these functions is exocytosis, bringing about the neurotransmitter release. If the release of transmitters is inhibited, the transmission of signals from cell to cell is blocked. For example, striated muscles are paralysed if the release of acetyl choline is inhibited at the neuromuscular contact point. This effect may be used therapeutically, if TrapoX is applied to nerve ends of spastic or dystonic muscles. Other active substances are, for example, substances exhibiting anti-viral action. Conjugated with Trapo, they might be of use for treating viral infections of the nervous system. The present invention also relates to the use of a transport protein for inhibiting the release of neurotransmitters.

If patients are treated with the native forms of BoNT/A and B, injection of these non-human proteins, despite the low dosage, causes the formation of antibodies, so that the therapy must be stopped in order to prevent anaphylactic shock. By applying a substance with the same active mechanism having a higher transport efficiency of the enzymatic activity, the dosage may be lowered drastically and the formation of antibodies will not occur. These properties are attributed to the transport protein described herein.

Although examples are stated for application, the suitable mode of application and the dosage is, in general, individually determined by the treating physician. Such decisions are routinely made by each physician well versed in the relevant special field. Thus, the mode of application and the dosage of the neurotoxin may e.g. be selected in accordance with the invention described herein, based on criteria such as the solubility of the selected neurotoxin or the intensity of the pain to be treated.

The treatment interval for native BoNT/A and B is currently three to four months on average. Prolonging this interval would reduce the risk of the formation of antibodies and allow a longer treatment period with BoNT. The increase of LC in the cytosol would extend its decomposition timewise and would thus also prolong the duration of action. The transport protein described here exhibits a higher affinity and reception rate than the native HC-A.

The following example merely serves for elucidation and should not be contemplated in a limiting manner.

EXAMPLES

Recombinant Expression of the Genetically Engineered TraPoX in *E. coli*

The DNA-sequence of the HC of BoNT/A was amplified in chromosomal DNA of *Clostridium botulinum* (database no. AAA23262 (SEQ ID NO: 1)) by means of PCR. For this purpose, by means of specific oligonucleotides, the codon for the amino acid tyrosine 1117 was substituted by a base triplet coding for the amino acid residue of alanine. Furthermore, the 5'-end of the gene was supplemented by a DNA-sequence, coding for the amino acids of the recognition sequence of thrombin. This DNA-sequence was inserted into a bacterial expression vector. The inserted gene for Trapo was in this case fused with an oligonucleotide at the 3'-end, coding for a carboxy-terminal affinity peptide such as e.g. the Strep-day, 6xHN-day (SEQ ID NO: 12) or $His_6$-day (SEQ ID NO: 13). The expression vector pAR-Trapo produced in this manner is the starting basis for adding carrier molecules, such as the LC of the BoNT.

The DNA-sequence of the LC of BoNT/A was amplified by the PCR-method in the chromosomal DNA-sequence of *Clostridium botulinum* (database no. AAA23262 (SEQ ID NO: 11) and inserted into the expression vector pAR-Trapo upstream of the coded thrombin recognition sequence. The expression vector pAR-TrapoX thus produced was transformed into an *E.coli* K12 strain and the expression of the protein TrapoX was induced under the conditions of Biological Safety Level 2 and in compliance with the rules and regulations issued for the project by the district government of Hanover, file reference 501g.40654/3/57/3. The over-expressed TrapoX was isolated in an affinity-chromatographic manner, following the directions of the manufacturer, as a single-chain protein with a molecular weight of 150 kDa. The protein was subsequently hydrolysed with thrombin conjugated on sepharose, bringing about a pure protein, the two chains of which remained interlinked by a disulphide-bridge.

Figure 1:
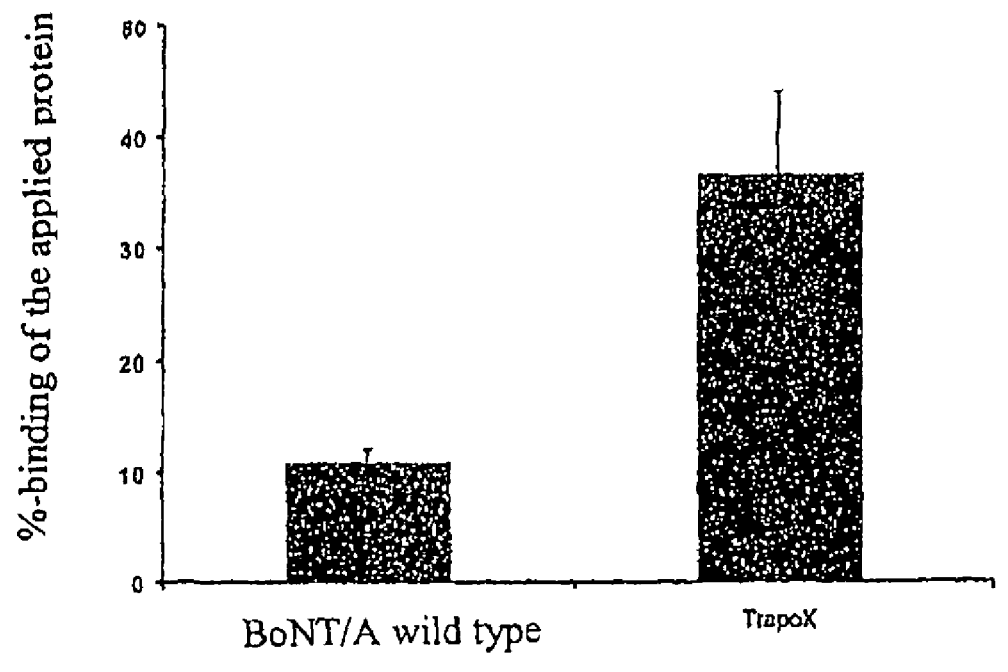

Compared with the wild type of BoNT/A, this protein exhibited an affinity, increased by 300%, to isolated ganglioside GT1b immobilised on micro titre plates and to synaptosome membrane preparations from rat brain (FIG. 1). The catalytic activity of the LC-A was not changed, as has been shown in the in vitro splitting of recombinant SNAP-25. The potency of the TrapoX with regard to inhibition of the neurotransmitter release in functional synaptosomes from rat brain had increased by 300%, compared with the native BoNT/A recovered from *Clostridium botulinum*. In nerve muscle-preparations of the mouse (HDA), the potency of the TrapoX was likewise increased by 300% compared with the native BoNT/A (FIG. 2).

Measurement of the Binding to Rat Brain Synaptosomes and the Neurotoxicity in the HDA of Different BoNT/A-mutants The binding of radioactively marked $H_C$-fragments to rat synaptosomes was measured as stated in Rummel et al., J. Mol. Biol. 326 (2003), 835-847. The neurotoxicity of the BoNT/A-mutants was determined as described by Habermann et al., Naunyn Schmiedeberg's Arch. Pharmacol. 311 (1980), 33-40.

The comparison of the binding of different BoNT/A-mutants as compared with the wild type is shown in the following table:

| Table relating to FIG. 2 | | |
| --- | --- | --- |
| Mutation | % vs. wild type | Standard deviation |
| Wild type | 100.0 | 15.00 |
| Y1117A | 332.3 | 29.00 |
| Y1117C | 324.2 | 44.75 |
| Y1117D | 124.4 | 26.94 |
| Y1117E | 183.3 | 27.95 |
| Y1117F | 235.9 | 38.41 |
| Y1117G | 112.8 | 21.34 |
| Y1117H | 120.0 | 22.29 |
| Y1117I | 248.1 | 21.95 |
| Y1117L | 253.6 | 25.65 |
| Y1117M | 182.8 | 18.41 |
| Y1117N | 250.3 | 20.13 |
| Y1117P | 150.3 | 14.98 |
| Y1117Q | 187.3 | 28.19 |
| Y1117R | 115.4 | 16.80 |
| Y1117S | 199.2 | 32.65 |
| Y1117T | 264.1 | 28.55 |
| Y1117V | 346.9 | 37.61 |
| F1252Y | 208.0 | 38.36 |
| H1253K | 153.0 | 9.24 |
| V1262I | 97.8 | 9.38 |
| Q1270N | 122.3 | 37.81 |

-continued

Table relating to FIG. 2

| Mutation | % vs. wild type | Standard deviation |
| --- | --- | --- |
| L1278H | 170.0 | 61.59 |
| G1279N | 153.6 | 44.54 |
| Y1117C/H1253K | 324.8 | 22.72 |
| Y1117V/H1253K | 332.9 | 33.48 |

The mutation of individual determined amino acids within the ganglioside binding pocket of BoNT/A resulted in an increase of the binding to nerve cells. Preferably, in position 1117, tyrosine is substituted by alanine, cysteine or valine. In particular, the substitution of the tyrosine residue in position 1117 by alanine results in an increase of the affinity to about 330%.

Further mutations of individual amino acids from the ganglioside binding pocket in position 1252 and 1253 result likewise in an increase of the binding. In particular, the mutation of F1252 in tyrosine and H1253 in lysine resulted in an increase of the affinity by 110%, and 50% respectively.

Furthermore, increases of the binding to nerve cells can be expected in mutations in positions 1202, 1262, 1270, 1278 and 1279.

Figure 2:
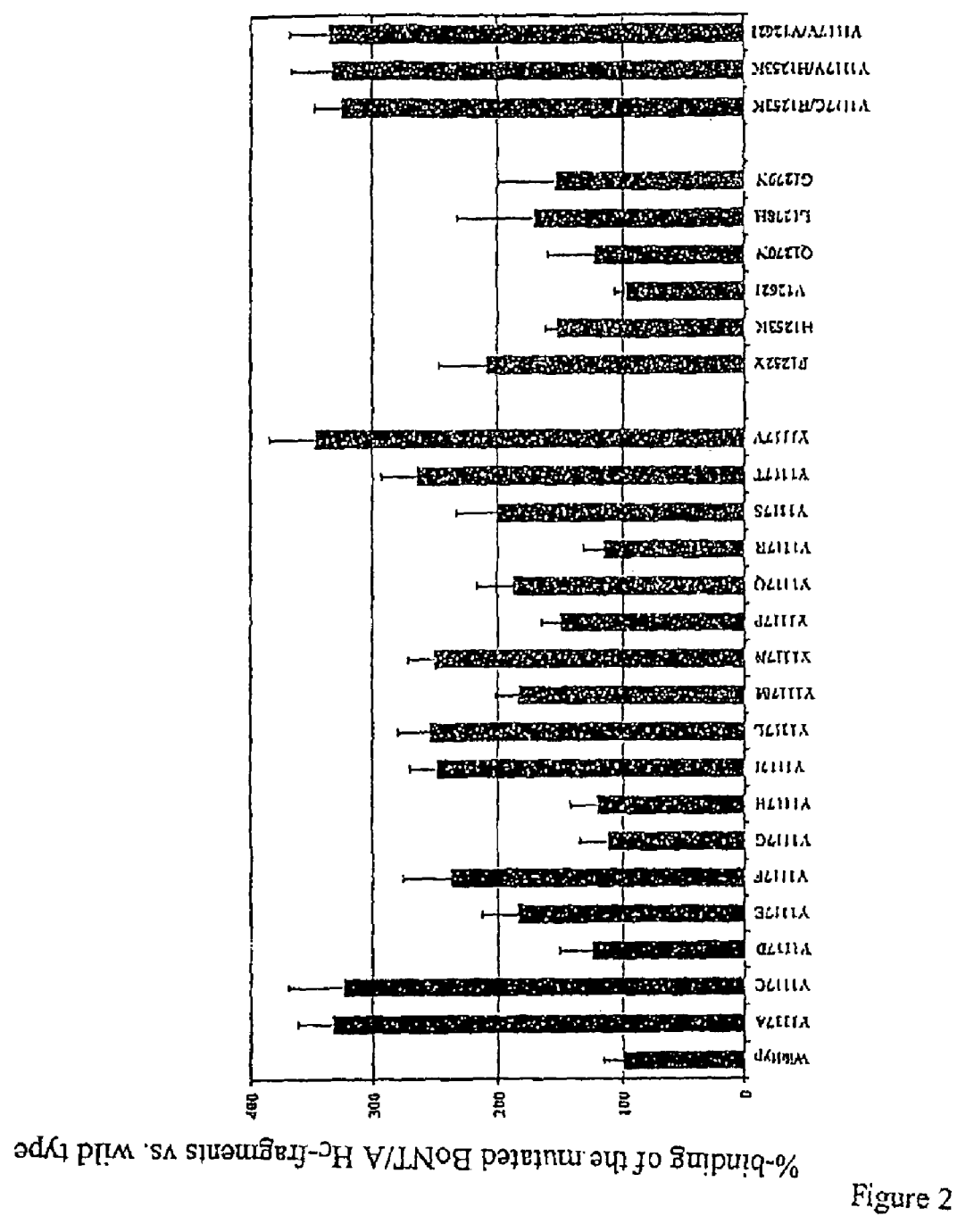

Moreover, mutants of BoNT/A were also tested with double mutations, in which case, in particular, the mutants Y1117C/H1253K and Y1117V/H1253K resulted in an increase of the binding to synaptosomes (cf. FIG. 2).

Figure 3:
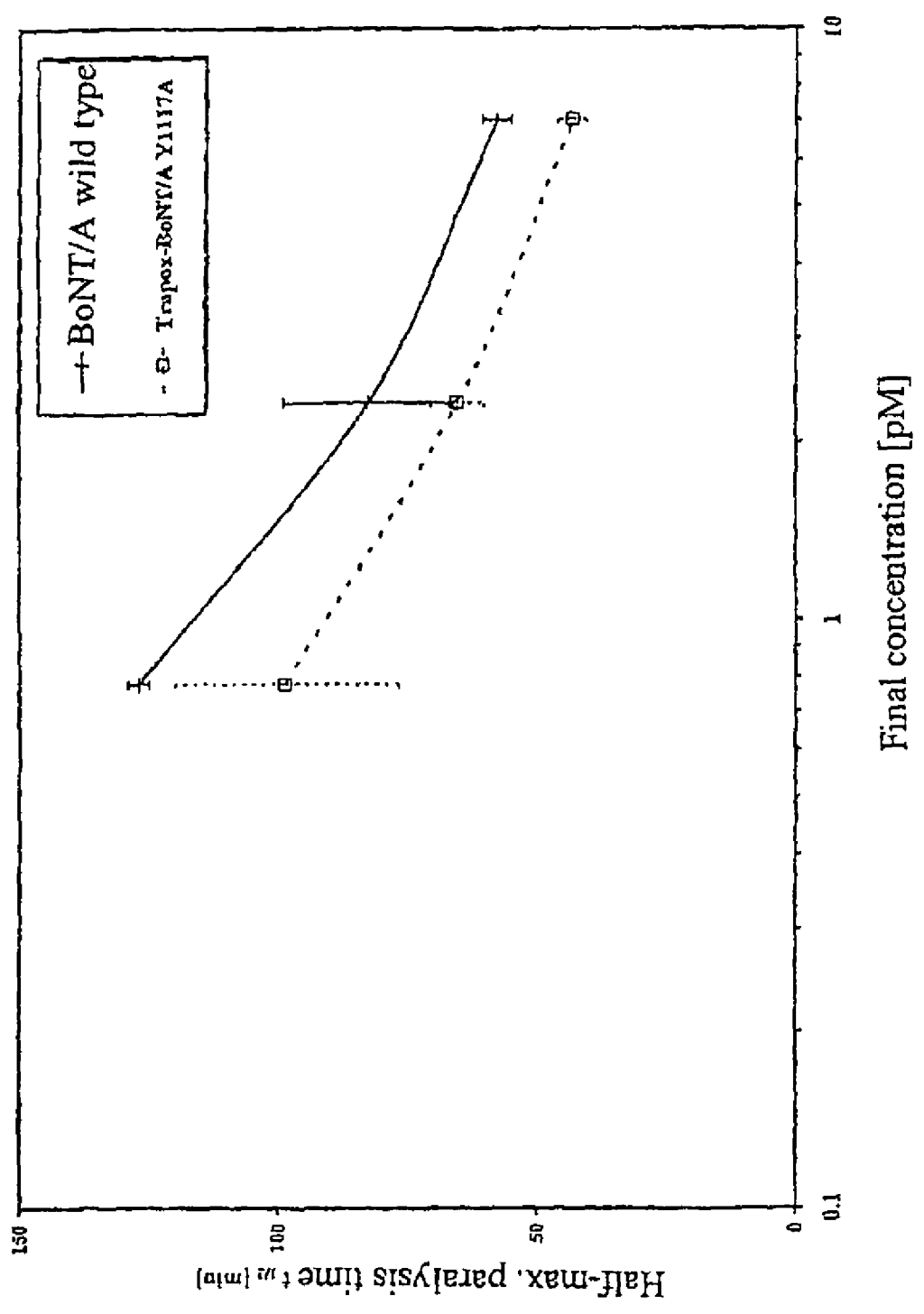

It was furthermore determined that the increase of the binding, particularly of the mutant Y1117A of BoNT/A resulted in an increase of the neurotoxicity in the N.phrenicus—neurotoxicity assay (HDA-Assay) (FIG. 3).

Determination of Binding and Neurotoxicity of BoNT/A $H_{CC}$-hybrids

The determination of the binding and the neurotoxicity was performed as described above.

The results are reflected in the following table and further in FIGS. 4 and 5.

Figure 4:
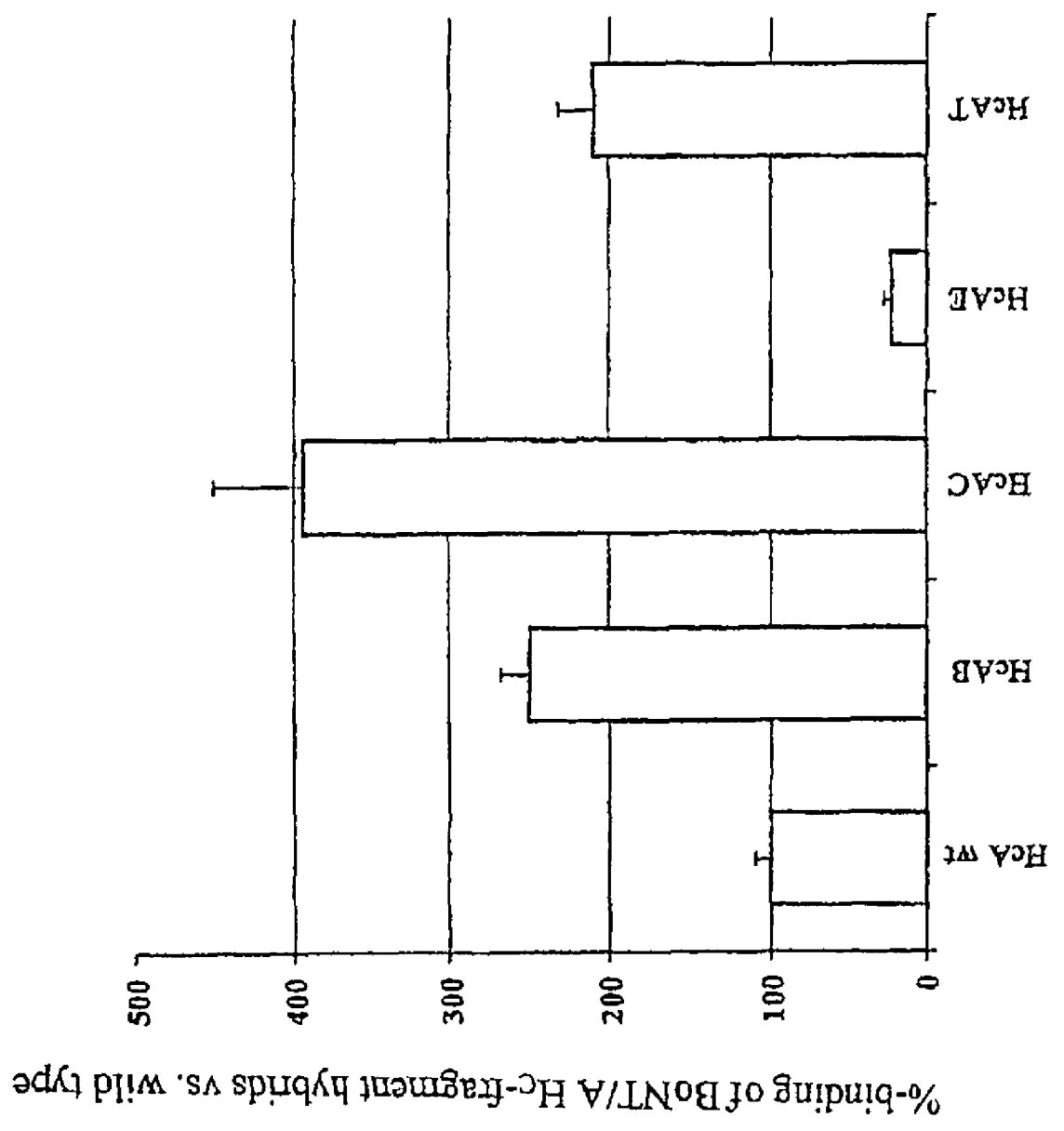

Table relating to FIG. 4

| Mutation | % vs. wild type | standard deviation |
| --- | --- | --- |
| HcA wt | 100.0 | 10.4 |
| HcAB | 249.2 | 19.1 |
| HcAC | 393.4 | 57.9 |
| HcAE | 22.0 | 5.3 |
| HcAT | 210.2 | 22.5 |

Substitution of the Hcc-domain of BoNT/A by the other serotypes, in particular *C. botulinum* neurotoxin B and C.

*botulinum* neurotoxin C, resulted in an increase of the binding to nerve cells. It was furthermore observed that the substitution of the $H_{CC}$-domain of $H_C$-fragment of BoNT/A by the corresponding domain of tetanus neurotoxin likewise resulted in an increase of the affinity in nerve cells. The affinity changes also apply to the substitution of the $H_{CC}$-domain in the entire BoNT/A. FIG. 5 shows in this context that in a hybrid scAtAAB the increase of affinity has a similar effect on increased neurotoxicity. If, instead of the $H_{CC}$-domain, the entire $H_C$-fragment scAtAAB is substituted, corresponding results are observed. In particular, it was observed that an improvement of the neurotoxicity by about 350% was noted when substituting the $H_{CC}$-domain or the $H_C$-fragment of BoNT/A by that of BoNT/B.

Determination of Binding of the BoNT-mutants to the Ganglioside GT1b

Ganglioside GT1b [NAcNeuα3Galβ3NAcGalβ4(NAcNeuα8NAcNeuα3)Galβ14Glcβ] (Sigma-Aldrich) is dissolved in methanol and applied to high-affinity 96-cup polystyrene-micro titre plates (Corning; 1 µg GT1b in 100 µl/cup) or, in the case of competition assays to high-affinity CS single fracture strip plates with $^{125}$I-BoNTs (Greiner Bioohne; 0,1 µg GT1b in 100 µl/cup). The solvent is evaporated at room temperature and the cups are rinsed three times with a binding buffer (10 mM Tris-HCl, 10 mM $Na_2HPO_4$, 0,5% BSA, pH7,2). The non specific binding sites are then blocked by incubation for two hours in PBSJTween [140 mM NaCl, 7 mM KCl, 10 mM $Na_2HPO_4$, 1,8 mM $KH_2PO_4$, 0,05% (VN) Tween 20, pH 7,2], supplemented by 3% (w/v) BSA. The binding assays are carried out in binding buffers (100 µl/cup) for 2 hours at room temperature either with increasing quantities of the wild type or specific quantities of the mutants. Unbound protein is removed in 3 rinsing steps, each with 250 µl PBS/Tween buffer. Bound $H_C$-fragments are identified by incubation with Strep Tactin conjugated with alkaline phosphatase (ST-AP, IBA GmbH) in a binding buffer for a duration of 2 hours at room temperature according to manufacturer's instructions. p-nitrophenyl phosphate (1 mg/ml in 100 mM glycine, 1 mM $MgCl_2$, 1 mM $ZnCl_2$, pH 10,4), which ultimately serves as substrate for the alkaline phosphatase. The desphorphorylation reaction is stopped by adding a 3 M NaOH solution and the extinction is measured at 405 nm using a Spectra Count micro plate reading device (Packard). The competition assays are performed over a period of 2 hours at room temperature in a 100 µl binding buffer with 700000 cpm/cup [1251]-BoNT, different quantities of native BoNT or recombinant $H_C$-fragment. After incubation and removal of the supernatants the cups are rinsed three times with PBS/Tween buffer, dried and separated. The quantities of bound radioactively marked BoNT are then determined in an automatic γ-counter (Wallac 1480 Wizard 3).

The invention claimed is:

1. An isolated, non-naturally occurring botulinum neurotoxin type A (BoNT/A) transport protein which binds to the nerve cells with a higher affinity than the native neurotoxin, wherein at least one amino acid of the native neurotoxin corresponding to positions 1117, 1252 and 1253 of the native botulinum neurotoxin type A protein sequence has been substituted by a naturally occurring amino acid, wherein the native botulinum neurotoxin type A protein sequence has protein database Accession Number AAA23262 (SEQ ID No. 1).

2. The transport protein according to claim 1, wherein the amino acid corresponding to position 1117 of the native botulinum neurotoxin type A protein sequence has been removed substituted by a naturally occurring amino acid.

3. The transport protein according to claim 2, wherein the amino acid corresponding to position 1117 of the native botulinum neurotoxin type A protein sequence has been substituted with an amino acid selected from the group consisting of alanine, cysteine, serine, threonine and valine.

4. The transport protein according to claim 2, wherein the amino acid corresponding to position 1117 of the native botulinum neurotoxin type A protein sequence has been substituted with an amino acid selected from the group consisting of alanine, cysteine and valine.

5. The transport protein according to claim 1, wherein the amino acid corresponding to position 1252 of the botulinum neurotoxin type A protein sequence is substituted by tyrosine or wherein the amino acid corresponding to position 1253 of the botulinum neurotoxin type A protein sequence is substituted by lysine.

6. The transport protein according to claim 1, wherein the protein binds specifically to nerve cells and enters the cells by endocytosis.

7. The transport protein according to claim 1, wherein the protein binds specifically to complex gangliosides of cholinergic motor neurons, localised in the plasma membrane, preferably GT1b.

8. A composition comprising a transport protein according to claim 1 and a protease, wherein the protease includes a light chain of a neurotoxin protein of *Clostridium botulinum* type A, B, C1, D, E, F or G, and wherein the protease and the transport protein are covalently bonded by an amino acid sequence, which is specifically recognized and split by an endopeptidase.

9. The composition according to claim 8, wherein after splitting by the endopeptidase a disulphide-bridge interlinks the protease and the transport protein, which, in turn, results in the formation of an active holotoxin.

10. The composition according to claim 8, wherein the protease has the sequence His-Glu-Leu-Xaa-His-(Xaa)$_{33-35}$-Glu-(Xaa)$_{84-90}$-Glu-(Xaa)$_{11}$-Arg-Xaa-Xaa-Tyr, wherein Xaa may be any amino acid (SEQ ID NO:11).

11. The composition according to claim 8, wherein the protease splits specific substrates within cholinergic motor neurons.

12. The composition according to claim 11, wherein the substrates are selected from proteins involved in the release of neurotransmitters in peripheral nerves, or from proteins capable of catalytic reactions within the nerve cell.

13. A pharmaceutical composition, comprising the composition according to claim 8, as well as optionally a pharmaceutically acceptable excipient, diluent and/or additive.

14. A cosmetic composition comprising the composition according to claim 8, as well as optionally a pharmaceutically acceptable excipient, diluent and/or additive.

15. A method for treating a disorder or disease for which a therapy with botulinum neurotoxin is indicated, said method comprising administration of an effective amount of the pharmaceutical composition according to claim 13.

16. A method of claim 15, wherein the disorder or disease is selected from the group consisting of hemi-facial spasm, spasmodic torticollis, spasticities, dystonias, migraine, pain, disorders of the neck-and lumber vertebral column, strabism, and hypersalivation.

17. A method for treating a cosmetic indication selected from hyperhydrosis and pronounced facial wrinkles, said method comprising administration of an effective amount of the cosmetic composition according to claim 14.

* * * * *